United States Patent [19]

Rosini et al.

[11] Patent Number: 5,191,125
[45] Date of Patent: Mar. 2, 1993

[54] PROCEDURE FOR THE PREPARATION OF BICYCLO [3.2.0]HEPT-2-EN-7-ONES

[75] Inventors: Goffredo Rosini, Bologna; Rossella Serra, Modena; Franco Rama, Varese; Giovanni Confalonieri, Milan, all of Italy

[73] Assignees: Enichem S.p.A., Milan; Istituto Guido Donegani S.p.A., Novara, both of Italy

[21] Appl. No.: 906,823

[22] Filed: Jun. 30, 1992

[30] Foreign Application Priority Data

Jul. 4, 1991 [IT] Italy .............................. 001855 A/91

[51] Int. Cl.$^5$ ............................................. C07C 45/45
[52] U.S. Cl. ..................................................... 568/356
[58] Field of Search ......................................... 568/356

[56] References Cited

U.S. PATENT DOCUMENTS 4,910,347 3/1990 Simmons ............................ 568/356

OTHER PUBLICATIONS

Beereboom, J. Org. Chem., vol. 30, pp. 4230–34 (1965).
Snider et al., J. Org. Chem., vol. 52, pp. 5413–19 (1987).
Snider et al., J. Org. Chem., vol. 53, pp. 5320–28 (1988).
Baeckstrom et al., J. Org. Chem., vol. 56, pp. 3358–62 (1991).

Primary Examiner—James H. Reamer
Attorney, Agent, or Firm—Oblon, Spivak, McClelland, Maier & Neustadt

[57] ABSTRACT

A procedure is described for the preparation of compounds having a bicyclo[3.2.0]heptenonic structure corresponding to the formula:

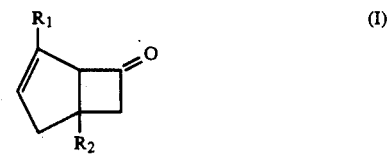

wherein $R_1$ and $R_2$, the same or different are hydrogen or a $C_1$-$C_4$ alkyl.

The compounds corresponding to formula (I) can be used as intermediates or precursors of pheromones, prostaglandins and antibiotics.

5 Claims, No Drawings

PROCEDURE FOR THE PREPARATION OF BICYCLO [3.2.0]HEPT-2-EN-7-ONES

The present invention relates to a process for the preparation of compounds having a bicyclo[3.2.0]heptenonic structure.

In particular it relates to a procedure for the preparation of bicyclo[3.2.0]hept-2-en-7-ones having the formula:

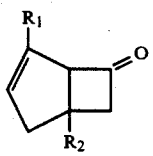

wherein $R_1$ and $R_2$, the same or different, are H or a $C_1$-$C_4$ alkyl group.

With respect to compounds having this structure, the known art mainly relates to the preparation of the isomeric compound bicyclo[3.2.0]hept-3-en-7-one having the formula:

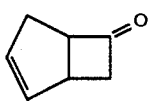

and its derivatives. These compounds are used as precursors or intermediates for the synthesis of products such as jasmonoids, prostaglandins and antibiotics.

Compounds corresponding to formula (I), although having valid requisites for being used as intermediates or precursors in organic synthesis, have proved to be more difficult to prepare.

I. Fleming et al. in Tetrahedron Supplement No.1 1981, page 13, describes the preparation of bicyclo[3.2.0]hept-2-en-7-one starting from the reaction of trimethylsilyl-cyclo-pentadiene with dichloroketene.7,7-dichloro-4-exo-trimethylsilyl-bicyclo[3.2.0] hept-2-en-6-one is obtained from which the product is obtained by means of dechlorination followed by a proto-desilylation reaction. With this method, however, it is not possible to prepare compounds substituted on the cyclopentenic ring.

B. B. Snider et al. in Journal of Organic Chemistry 1988, vol.53, page 5320, describes the reaction of chlorides of unsaturated α,β-acids with triethylamine in benzene under reflux conditions using the high dilution technique. A 1:1 mixture of α,β-unsaturated cis- and trans-ketenes is obtained. When a second unsaturation is present in the side chain, the cis isomer undergoes an intramolecular cycloaddition to generate a bicyclo[3.2.0]hept-3-en-6-one and/or a bicyclo[3.2.0]hept-2-en-6-one with overall yields of 30-50%. If the above acyl chlorides are β,β-disubstituted, B. B. Snider et al. in Journal of Organic Chemistry 1987, vol.52, page 5413, claims that isomers with a double exocyclic bond are basically obtained.

The results of the research carried out by Snider et al. on this subject are contained in Chem. Rev., vol.88, page 793, 1988.

J. J. Beereboom in Journal of Organic Chemistry 1965, vol.30, page 4230, describes the cyclization reaction of a mixture of cis- and trans-geranic acids in the presence of acetic anhydride and sodium acetate under reflux conditions. The corresponding bicyclo[3.2.0]hept-2-en-7-one is however mixed with other products with a yield of only 28%.

P. Baeckstrom e al. in Journal of Organic Chemistry 1991, vol.56, page 3358, describes a process for the preparation of lineatine, which includes a similar reaction to that of Beereboom, carried out on a mixture of acids, from which the desired bicyclo[3.2.0]hept-2-en-7-one is obtained with a yield of 42%, together with 21% of an isomer with a double exocyclic bond. Treatment on activated Pd/C catalyst with hydrogen is required to transform this latter into the desired isomer.

The purpose of the present invention is consequently to present an improved procedure for the preparation of compounds corresponding to formula (I), which, as well as increasing the yields of the product, also guarantees greater operational simplicity and improved selectivity and stereospecificity.

This and other objectives are obtained according to the invention by means of a procedure for the preparation of bicyclo[3.2.0]hept-2-en-7-ones having the formula:

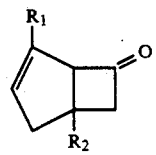

wherein $R_1$ and $R_2$, the same or different, are H or a $C_1$-$C_4$ alkyl group, including:

(a) the reaction of a 3-hydroxy-6-alkenoic acid having the formula:

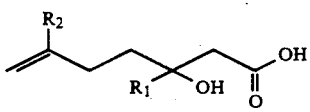

wherein $R_1$ and $R_2$ have the above meaning, with sodium or potassium acetate and with acetic anhydride, carried out at room temperature for a period of at least two hours, (b) treatment at a temperature ranging from 100° to 140° C., under reflux conditions, for a period which is sufficient to complete the reaction, and (c) separation of the product (I) from the reaction mixture. $R_1$ and $R_2$, the same or different, are preferably H or $CH_3$.

The temperature of step (b) preferably ranges from 115° to 125° C.

The treatment of step (b) is preferably carried out for a period of two to eight hours.

The reactive process of the invention does not require the use of catalysts or inert solvents.

The molar ratios between the reagents may vary within a wide range. It is convenient to use ratios acid/anhydride/acetate of 1:9:2.

Mixtures are obtained from step (b) from which the product can be recovered using the normal separation techniques. It is advisable to carry out a preliminary hydrolysis of the acetic anhydride at room temperature, in the presence of solvents such as light petroleum ether, under stirring for 4-12 hours, to remove the products from the water-acetic acid phase by extraction.

The bicyclo[3.2.0]hept-2-en-7-one obtained with the procedure of the present invention has basically no isomer with a double exocyclic bond. Any possible traces of this may be separated from the desired isomer by means of flash chromatography with petroleum ether/ethyl ether in a ratio of 95:5, as eluant mixture.

The 3-hydroxy-6-alkenoic acids corresponding to formula (III) can be prepared by means of a Reformatsky reaction between an unsaturated ketone, or aldehyde, corresponding to formula (IV) and a bromoacetate corresponding to formula (V), carried out in the presence of zinc and followed by the saponification of intermediate ester (VI). The scheme of the reaction is shown below:

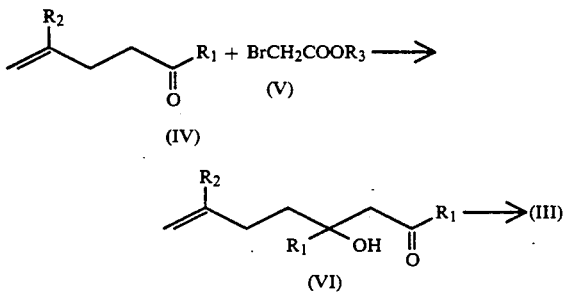

wherein $R_1$ and $R_2$ have the above-defined meaning, and $R_3$ is methyl, ethyl or isopropyl group.

Another method for preparing the acids corresponding to formula (III) consists of the reduction of β-ketoesters corresponding to formula (VII), carried out with sodium borohydride in methanol at a temperature below 0° C. and followed by the saponification of the intermediate ester (VI). The scheme of the reaction is shown below:

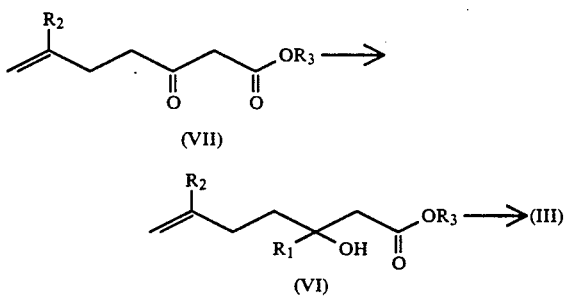

wherein $R_1$ is H, and $R_2$ and $R_3$ have the above-defined meaning.

Examples of compounds obtained from the procedure of the present invention are:
bicyclo[3.2.0]hept-2-en-7-one,
2-methyl-bicyclo[3.2.0]hept-2-en-7-one,
5-methyl-bicyclo[3.2.0]hept-2-en-7-one,
2,5-dimethyl-bicyclo[3.2.0]hept-2-en-7-one.

The bicyclo[3.2.0]hept-2-en-7-ones obtained from the procedure of the present invention, owing to the typical reactivity of the cyclobutanonic system contained in a bicyclic structure, can give rise to reactions such as stereoselective reduction to the corresponding endo-alcohol, alkylation at the carbonylic carbon, derivatization of the latter, ring expansion with diazomethane and similar products, Bayer-Villiger stereospecific lactonization reactions.

Moreover, owing to the potentiality linked to the pentaatomic cyclic system with the olefinic residue, reactions can be carried out such as hydrogenation, epoxidation, hydroxylation, bis-hydroxylation and oxidative fragmentation, as well as conversion to halohydrines and to derivatives of the alkyl type.

The above products can consequently put to advantageous use as intermediates or precursors in the synthesis of compounds such as pheromones, jasmonoids, prostaglandins and antibiotics.

In particular, the compound having formula (I) wherein $R_1$ and $R_2$ are $CH_3$, i.e. 2,5-dimethyl-bicyclo[3.2.0]hept-2-en-7-one, constitutes a useful intermediate for the preparation of two pheromones of considerable importance: lineatine (P. Baeckstrom e al., Journal of Organic Chemistry 1991, vol.56, page 3358) and grandisol (G. Rosini e al., Tetrahedron vol.41, No.20, page 4633, 1985).

In addition, the compound having formula (I) wherein $R_1$ and $R_2$ are hydrogen, i.e. bicyclo[3.2.0]hept-2-en-7-one, can be conveniently used as a starting product for the synthesis of Brefeldin A, a substance having biological activity, such as for example, antibiotic, antiviral, cytostatic and antimycotic (E. J. Corey e al., Tetrahedron Letters, vol.31, page 75, 1990, and references cited therein).

The procedure of the present invention consequently provides a new means of access to an important class of compounds, and is characterized by its operational simplicity, economy of the reagents and required equipment, as well as considerably improved yields and selectivity compared to the procedures of the known art. The following examples provide a better illustration of the present invention but do not limit it in any way.

EXAMPLE 1

Preparation of 2,5-dimethyl-bicyclo[3.2.0]hept-2-en-7-one 8.49 g (0.05 moles) of 3,6-dimethyl-3-hydroxy-hept-6-enoic acid, 40 ml of acetic anhydride and 10 g of potassium acetate are charged into a 100 ml flask equipped with a reflux condenser fitted with a $CaCl_2$ tube.

The reaction mixture is left at room temperature under stirring for two hours. The temperature is then brought to 120° C. and the mixture is kept under reflux for four hours. At this stage the mixture is poured into a 250 ml flask, light petroleum ether (45°-50° C.) and water are added, and the mixture is kept under stirring overnight at room temperature.

The organic fraction is separated by means of a separating funnel, washed with an aqueous solution of sodium bicarbonate and then dried over sodium sulphate. The solvent is removed by evaporation at reduced pressure.

A crude product is obtained, which, after distillation under vacuum, provides a mixture of 2,5-dimethyl-bicyclo[3.2.0]hept-2-en-7-one and its isomer having the double exocyclic bond in a ratio of 98:2. The yield, after distillation, is 82%.

The product was characterized by means of IR, $^1$H-NMR and $^{13}$C-NMR spectroscopy.

EXAMPLE 2

Preparation of bicyclo[3.2.0]hept-2-en-7-one.

2.73 g (0.019 moles) of 3-hydroxy-hept-6-enoic acid, 20 ml of acetic anhydride and 4 g of potassium acetate are charged into a 50 ml flask equipped with a reflux condenser fitted with a CaCl₂ tube. The mixture is treated under the same conditions as Example 1.

A crude product is obtained from which, after purification by silica gel column chromatography, bicyclo[3.2.0]hept-2-en-7-one is obtained. The yield, after chromatography, is 57%.

The product was characterized by IR, ¹H-NMR and ¹³C-NMR spectroscopy.

EXAMPLE 3

Preparation of 2-methyl-bicyclo[3.2.0]hept-2-en-7-one 2.07 g (0.013 moles) of 3-methyl-3-hydroxy-hept-6-enoic acid, 15 ml of acetic anhydride and 3 g of potassium acetate are charged into a 50 ml flask equipped with a reflux condenser fitted with a CaCl₂ tube.

The mixture is treated under the same conditions as Example 1.

A crude product is obtained from which, after purification by silica gel column chromatography,2-methyl-bicyclo[3.2.0]hept-2-en-7-one uncontaminated by its isomer with a exocyclic double bond, is obtained. The yield, after chromatography, is 79%.

The product was characterized by means of IR, ¹H-NMR and ¹³C-NMR spectroscopy.

EXAMPLE 4

Preparation of 5-methyl-bicyclo[3.2.0]hept-2-en-7-one 2.56 g (0.016 moles) of 6-methyl-3-hydroxy-hept-6-enoic acid, 20 ml of acetic anhydride and 4 g of potassium acetate are charged into a 100 ml flask equipped with a reflux condenser fitted with a CaCl₂ tube.

The mixture is treated under the same conditions as Example 1.

A crude product is obtained from which, after purification by silica gel column chromatography, 5-methyl-bicyclo[3.2.0]hept-2-en-7-one is obtained. The yield, after chromatography, is 31%.

The product was characterized by means of IR, ¹H-NMR and ¹³C-NMR spectroscopy.

We claim:
1. Procedure for the preparation of bicyclo[3.2.0]hept-2-en-7ones having the formula:

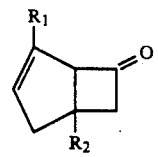

wherein $R_1$ and $R_2$, the same or different, are H or a $C_1-C_4$ alkyl group, including:
(a) the reaction of a 3-hydroxy-6-alkenoic acid having the formula:

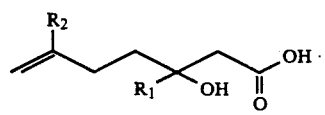

wherein $R_1$ and $R_2$ have the above meaning, with sodium or potassium acetate and acetic anhydride, carried out at room temperature for a period of at least two hours,
(b) treatment at a temperature ranging from 100° to 140° C., under reflux conditions, for a period which is sufficient to complete the reaction, and
(c) separation of the product (I) from the reaction mixture.

2. Procedure according to claim 1, wherein the treatment in step (b) is carried out for a period of two to eight hours.

3. Procedure according to claim 1, wherein $R_1$ and $R_2$ are $CH_3$.

4. Procedure according to claim 1, wherein $R_1$ and $R_2$ are H.

5. Procedure according to one or more of the previous claims, wherein the temperature in step (b) ranges from 115° to 125° C.

* * * * *